United States Patent

Koike et al.

[11] Patent Number: 5,773,265
[45] Date of Patent: Jun. 30, 1998

[54] DNA ENCODING HEPTAPRENYL DIPHOSPHATE SYNTHETASE

[75] Inventors: Ayumi Koike, Toyota, Japan; Shusei Obata, New York, N.Y.; Kyozo Ogura; Tanetoshi Koyama, both of Sendai, Japan

[73] Assignee: Toyota Jidosha Kabushiki Kaisha, Toyota, Japan

[21] Appl. No.: 506,404

[22] Filed: Jul. 24, 1995

[30] Foreign Application Priority Data

Jul. 29, 1994 [JP] Japan ..................................... 6-179336

[51] Int. Cl.$^6$ .............................. C12P 9/00; C12P 21/06; C12N 9/10; C07H 21/04
[52] U.S. Cl. ..................... 435/131; 435/69.1; 435/172.3; 435/193; 435/252.3; 435/252.33; 435/320.1; 435/832; 536/23.2
[58] Field of Search ................................... 435/69.1, 131, 435/252.3, 172.3, 252.33, 193, 320.1, 832; 536/23.2

[56] References Cited

FOREIGN PATENT DOCUMENTS 0 674 000 A2   9/1995   European Pat. Off. .

OTHER PUBLICATIONS

Ohnuma, et al., *J. Biol. Chem.*, 269:20, May 20 1994, pp. 14792–14797.
J. Biol. Chem. 225, pp. 4539–4543 (1980).
J. Biol. Chem. 265, pp. 4607–4614 (1990).
Proc. Natl. Acad. Sci. USA, pp. 6761–6764 (1992).
FEBS Lett. 161, pp. 257–260 (1983).
Summary of 67th Meeting of Japanese Biochemical Society No. 1728 (1994) (English Translation).
Summary of 17th Meeting of Japanese Molecular Biology Society (1994) (English Translation).
J. Biochem., 113:3, pp. 355–363, Mar. 1993, Tokyo JP, "Thermostable Farnesyl Diphosphate Synthase . . . Overproduction and Purification", T. Koyama, et al. (Abstract).
FEBS Letters, 161:2, pp. 257–260, Sep. 19, 1983, Amsterdam NL, "Essential Protein Factors for Polyprenyl Pyrophosphase Synthetases . . . ", H. Fuji, et al.
J. Biochem., 270:31, pp. 18396–18400, Aug. 1995, Maryland US, "Molecular Cloning and Nucleotide Sequences . . . Heptaprenyl Diphosphate Synthesis", A. Koike–Takeshita, et al.
Koyama et al. (1994) Tennen Yuki Kagobutsu Toronkai Koen Yoshishu, 36th, 167–174 (abstract).

*Primary Examiner*—Robert A. Wax
*Assistant Examiner*—Elizabeth Slobodyansky
*Attorney, Agent, or Firm*—Kenyon & Kenyon

[57] ABSTRACT

Heptaprenyl diphosphate (HDP)-synthetase derived from *Bacillus stearothermophilus* which enzymes have the amino acid sequences shown as SEQ ID NOs: 1 to 3; 1 and 2; 2 and 3; or 1 and 3, DNA encoding them, and a method of producing the enzymes.

According to the invention it is possible to industrially produce HDP-synthesizing enzyme and HPD.

13 Claims, 2 Drawing Sheets

DNA ENCODING HEPTAPRENYL DIPHOSPHATE SYNTHETASE

BACKGROUND OF INVENTION

1. Field of Invention

The present invention relates to heptaprenyl diphosphate (hereunder sometimes abbreviated to "HDP") synthetase of *Bacillus stearothermophilus* origin, to DNA encoding the enzyme, to an expression vector containing the DNA, to a host transformed by the expression vector, to a method of producing heptaprenyl diphosphate-synthesizing enzyme by the host, and to a method of producing heptaprenyl diphosphate using the enzyme or host.

2. Related Art

HDP, synthesized from condensation reaction of 4 molecules of isopentenyl diphosphate and 1 molecule of farnesyl diphosphate by HDP-synthetase, is an important biosynthetic intermediate of isoprenoids such as prenylquinone. Although HDP-synthetase, which is categorized into prenyl transferase, is known to be present in some microorganisms such as *Bacillus subtilis* (J. Biol. Chem. 255, p.4539–4543 (1980)), its amino acid sequence and the DNA sequence of the gene encoding it have not been known.

Genes coding for other prenyl transferase are known, farnesyl diphosphate synthetase ([2.5.1.1.] J. Biol. Chem. 265, p.4607–4614 (1990)), geranylgeranyl diphosphate synthetase (Proc. Natl. Acad. Sci. USA, 89, p.6761–6764). However, the tertiary structures of the known prenyl transferases are homodimers which comprise two identical subunits, and it is different from the peculiar heterodimer of *Bacillus subtilis* HDP synthetase (FEBA Letl. 161, 257–260 (1983)). Therefore, absolutely no data exists regarding homology between the amino acid sequences of the former two and the latter.

Consequently, the present invention is aimed at providing HDP synthetase of *Bacillus stearothermophilus* origin, which was hitherto unknown in the species, DNA encoding the enzyme, and a method of production of the recombinant HDP synthetase using the DNA.

SUMMARY OF INVENTION

With the aim of accomplishing the above-mentioned object, the present inventors have been the first to succeed in cloning an HDP synthetase gene of *Bacillus stearothermophilus* origin, by the PCR method using synthesized primers designed from a portion of the known sequence of prenyl transferase, following hybridization using PCR amplified fragments as probe and measuring the expressed activity of the gene expression products.

Thus, the present invention provides a protein of *Bacillus stearothermophilus* origin having heptaprenyl diphosphate synthetase activity, which comprises a peptide with the amino acid sequence from the 1st amino acid Met to the 220th amino acid Gly of Sequence No. 1 (SEQ ID NO:1), or an amino acid sequence resulting from a substitution, deletion or addition of one or a few amino acids in the amino acid sequence; a peptide with the amino acid sequence from the 1st amino acid Met to the 234th amino acid Arg of Sequence No. 2 (SEQ ID NO:2), or an amino acid sequence resulting from a substitution, deletion or addition of one or a few amino acids in the amino acid sequence; and a peptide with the amino acid sequence from the 1st amino acid Val to the 323rd amino acid Tyr of Sequence No. 3 (SEQ ID NO:3), or an amino acid sequence resulting from a substitution, deletion or addition of one or a few amino acids in the amino acid sequence.

The present invention also provides a peptide of *Bacillus stearothermophilus* origin, which has the amino acid sequence from the 1st amino acid Met to the 220th amino acid Gly of Sequence No. 1 (SEQ ID NO:1), or an amino acid sequence resulting from a substitution, deletion or addition of one or a few amino acids in the amino acid sequence.

The present invention further provides a peptide of *Bacillus stearothermophilus* origin, which has the amino acid sequence from the 1st amino acid Val to the 323rd amino acid Tyr of Sequence No. 3 (SEQ ID NO:3), or an amino acid sequence resulting from a substitution, deletion or addition of one or a few amino acids in the amino acid sequence.

The present invention further provides a protein of *Bacillus stearothermophilus* origin with heptaprenyl diphosphate synthetase activity, which comprises a peptide with the amino acid sequence from the 1st amino acid Met to the 220th amino acid Gly of Sequence No. 1 (SEQ ID NO:1), or an amino acid sequence resulting from a substitution, deletion or addition of one or a few amino acids in the amino acid sequence; and a peptide with the amino acid sequence from the 1st amino acid Val to the 323rd amino acid Tyr of Sequence No. 3 (SEQ ID NO:3), or an amino acid sequence resulting from a substitution, deletion or addition of one or a few amino acids in the amino acid sequence.

The present invention further provides a protein of *Bacillus stearothermophilus* origin with heptaprenyl diphosphate synthetase activity, which comprises a peptide with the amino acid sequence from the 1st amino acid Met to the 220th amino acid Gly of Sequence No. 1 (SEQ ID NO:1), or an amino acid sequence resulting from a substitution, deletion or addition of one or a few amino acids in the amino acid sequence; and a peptide with the amino acid sequence from the 1st amino acid Met to the 234th amino acid Arg of Sequence No. 2 (SEQ ID NO:2), or an amino acid sequence resulting from a substitution, deletion or addition of one or a few amino acids in the amino acid sequence.

The present invention further provides a protein of *Bacillus stearothermophilus* origin with heptaprenyl diphosphate synthetase activity, which comprises a peptide with the amino acid sequence from the 1st amino acid Met to the 234th amino acid Arg of Sequence No. 2 (SEQ ID NO:2), or an amino acid sequence resulting from a substitution, deletion or addition of one or a few amino acids in the amino acid sequence; and a peptide with the amino acid sequence from the 1st amino acid Val to the 323rd amino acid Tyr of Sequence No. 3 (SEQ ID NO:3), or an amino acid sequence resulting from a substitution, deletion or addition of one or a few amino acids in the amino acid sequence.

The present invention further provides DNA encoding the above-mentioned protein and various peptides.

The present invention further provides an expression vector comprising the above-mentioned DNA.

The present invention further provides a host transformed by the above-mentioned expression vector.

The present invention further provides a method of producing heptaprenyl diphosphate synthetase which is characterized by culturing the above-mentioned host, and collecting heptaprenyl diphosphate synthetase from the cultured product.

The present invention further provides a method of producing heptaprenyl diphosphate which is characterized by culturing the above-mentioned transformant, and collecting heptaprenyl diphosphate from the cultured product.

The present invention further provides a method of producing heptaprenyl diphosphate which is characterized by reacting the above-mentioned enzyme with a substrate.

DETAILED DESCRIPTION

The open reading frame portions of nucleotide sequences of DNA cloned from *Bacillus stearothermophilus* which express heptaprenyl diphosphate synthetase activity are shown as SEQ ID NOs: 1 to 3. There are 3 open reading frames (ORF). The first open reading frame (ORFI) is assumed to begin at the ATG coding for the 1st amino acid Met of SEQ ID NO: 1 and to end with the GGG coding for the 220th Gly. However, it may possibly begin at the ATG coding for the 19th amino acid Met, the ATG coding for the 20th amino acid Met, or the ATG coding for the 22nd amino acid Met.

The second open reading frame (ORFII) is assumed to begin at the ATG coding for the 1st amino acid Met of SEQ ID NO: 2 and to end with the CGG coding for the 234th amino acid Arg. However, this ORFII may possibly begin at the ATG coding for the 23rd amino acid Met of the amino acid sequence. The third open reading frame (ORFIII) is assumed to begin at the GTG coding for the 1st amino acid Val of SEQ ID NO: 3, and to end with the TAT coding for the 323rd amino acid Tyr. However, this ORFIII may possibly begin at the ATG coding for the 4th amino acid Met or the ATG coding for the 9th amino acid Met.

In the DNA containing the cloned ORFI–III, the nucleotide AACG is located between the translation termination codon TAG at the 3' end of ORFI and the translation initiation codon ATG (Met) of ORFII, and the nucleotide GTTAAG is located between the translation termination codon TGA of ORFII and the translation initiation codon GTG (Val) of ORFIII.

The full-length DNA expression product had the strongest heptaprenyl diphosphate synthetase activity and the expression products of ORFI and ORFIII, ORFI and ORFII, and ORFII and ORFIII also showed heptaprenyl diphosphate synthetase activity. Consequently, according to one embodiment of the present invention, there are provided DNA comprising all of ORFI, ORFII and ORFIII, heptaprenyl diphosphate synthetase consisting of the peptide encoded thereby, and a method for its production.

The present invention also provides DNA containing ORFI and ORFIII but not containing ORFII in its complete form, a peptide having heptaprenyl diphosphate synthetase activity which is expressed by that DNA, and a method for its production. The present invention further provides DNA containing ORFI and ORFII, or ORFII and ORFIII but not containing any other ORF in its complete form, a peptide expressed thereby, and a method for its production.

Plant-derived enzymes sometimes differ in a few amino acids depending on the variety of plants from which they are derived, and often differ in a few amino acids by natural mutations. In addition, the native activity of an enzyme is sometimes maintained even upon artificial mutation on the amino acid sequence. Consequently, the present invention also encompasses, in addition to peptides having the amino acid sequences represented by SEQ ID NOs: 1 to 3, also peptides with amino acid sequences resulting from variations of the amino acid sequences represented by SEQ ID NOs: 1 to 3 by means of a substitution, deletion and/or addition of one or a few, for example 5 or 10, amino acids, providing that the peptides are still have the enzyme activity.

The present invention further provides DNA encoding a peptide mutated in the manner described above, as well as a method of producing the mutated peptide.

As will be explained in detail by way of the examples, the DNA of the present invention may be cloned from *Bacillus stearothermophilus*. Also, DNA containing any one of ORFI, ORFII and ORFIII, all three, or ORFI and ORFIII, ORFI and ORFII or ORFII and ORFIII, and not containing any other ORF in its complete form, may be obtained by cutting full-length DNA using restriction endonucleases which cut within, for example, other ORFs outside of the aimed ORF without cutting within the latter. Alternatively, DNA encoding a mutated peptide may be obtained by the site-specific mutagenesis using, for example, a mutagenic primer.

Furthermore, once the amino acid sequence of one peptide is determined, it is possible to define a proper nucleotide sequence coding therefor, which then allows chemical synthesis of the DNA by conventional DNA synthesis methods. Each individual ORF of the present invention is not especially long, and thus may be easily synthesized by a person skilled in the art by conventional DNA synthesis methods.

The present invention further provides expression vectors comprising the DNA as described above, hosts transformed by the expression vectors, and a method of producing the enzyme or peptides of the present invention using these hosts.

The expression vector includes an origin of replication, the expression regulating sequence, etc., which differ depending on the host. The host may be a prokaryotic organism, for example a bacterium such as an *E. coli*, or Bacillus such as *Bacillus subtilis*; a eukaryotic organism, for example yeast, a fungus an example of which is *S. cerevisiae* belonging to the genus Saccharomyces, or fungus an example of which is a mold such as *A. niger* or *A. oryzae* belonging to the genus Aspergillus; animal cells such as cultured silk worm cells or cultured higher animal cells, for example CHO cells. Plant cells may also be used as hosts.

According to the present invention, as will be shown in the examples, it is possible to produce heptaprenyl diphosphate synthase by culturing a host transformed with DNA of the present invention, which accumulates the enzyme in the culture, and recovering it. Also, according to the present invention, heptaprenyl diphosphate may also be produced by allowing HDP synthetase produced by the method of the present invention to react with isopentenyl diphosphate and allylic diphosphate such as farnesyl diphosphate acid as substrates.

Referring to the use of *E. coli* as a host for an example, there are known gene expression regulating mechanism in the process of transcription of mRNA from DNA, the process of translation of protein from mRNA, etc. As promoter sequences which regulate mRNA synthesis, there are known, in addition to naturally occurring sequences (for example, lac, trp, bla, lpp, $P_L$, $P_R$, ter, T3, T7, etc.), also mutants thereof (for example, lacUV5) and sequences obtained by artificially fusing natural promoter sequences (for example, tac, trc, etc.), and these may also be used according to the present invention.

As sequences capable of regulating ability to synthesize protein from mRNA, the importance of the ribosome-binding site (GAGG and similar sequences) and the distance to the initiation codon ATG is already known. It is also well known that terminator sequences which govern completion of transcription at the 3' end (for example, vectors including rrnBT$_1$T$_2$ are commercially available from Pharmacia Co.) affect the efficiency of protein synthesis in recombinants.

Vectors which may be used to prepare the recombinant vectors of the present invention may be commercially available ones, or they may be any of a variety of derived vectors, depending on the purpose. As examples there may be mentioned pBR322, pBR327, pKK223-3, pKK233-2, pTrc99, etc. which carry the pMB1-derived replicon; pUC18, pUC19, pUC118, pUC119, pHSG298, pHSG396, etc. which have been modified for increased number of copies; pACYC177, pACYC184, etc. which carry the p15A-derived replicon; and plasmids derived from pSC101, ColE1, R1 or F factor.

In addition to plasmids, gene introduction is also possible by way of virus vectors such as λ-phage and M13 phage, and transposons. For gene introduction to microorganisms other than *E. coli*, there is known gene introduction to the genus Bacillus by pUB110 (available from Sigma Co.) and pHY300PLK (available from Takara Shuzo). These vectors are described in *Molecular Cloning* (J. Sambrook, E. F. Fritsch, T. Maniatis, published by Cold Spring Harbor Laboratory Press), *Cloning Vector* (P. H. Pouwels, B. E. Enger/Valk, W. J. Brammar, published by Elsevier), and various company catalogs.

In particular, pTrc99 (available from Pharmacia Co.) is preferred as a vector including, in addition to the ampicillin resistance gene as a selective marker, Ptrc and lacIq as a promoter and controlling gene, the sequence AGGA as a ribosome-binding site, and rrnBT$_1$T$_2$ as the terminator, and having an expression regulating function on the HDP-synthesizing enzyme gene.

The incorporation into these vectors of a DNA fragment coding for HDP synthetase and if necessary a DNA fragment with the function of expression regulation on the gene for the above-mentioned enzyme, may be accomplished by a known method using an appropriate restriction endonuclease and ligase. Specifically the method described below may be conveniently followed. pTL6 may be mentioned as a definite plasmid of the present invention prepared in this manner.

As microorganisms for the gene introduction by such recombinant vectors, there may be used *Escherichia coli*, as well as microorganisms belonging to the genus Bacillus. The transformation may also be carried out by a conventional method, for example the CaCl$_2$ method or protoplast method described in *Molecular Cloning* (J. Sambrook, E. F. Fritsch, T. Maniatis, published by Cold Spring Harbor Laboratory Press) or *DNA Cloning Vol.I–III* (ed. by D. M. Glover, published by IRL PRESS), etc.

A representative transformant according to the present invention which may be obtained is pTL6/JM109.

When these transformants or recombinant microorganism cells are cultured in medium normally used for *E. coli*, heptaprenyl diphosphate synthase (HDP synthase) accumulates in the cells. The HDP in the cells may be recovered by physical treatment in the absence or presence of a cytolytic enzyme for lysis and a conventional isolation and purification method for enzymes.

Lysozyme is preferably used as the cytolytic enzyme, and ultrasonic waves are preferably used for physical treatment. Most of the *E. coli*-derived protein may be removed as insoluble deposit by heating at about 55° C. For the isolation and purification of the enzyme, any or a combination of gel filtration, ion exchange, hydrophobic, reverse phase, affinity or other type of chromatography, or ultrafiltration may be available.

During the process of isolation and purification, a reagent to stabilize the desired enzyme may be combined with the treatment solution, for example, a reducing agent such as β-mercaptoethanol or dithiothreitol, protective agent against proteases, such as PMSF or BSA, or metal ion such as magnesium.

Since the above-mentioned HDP synthetase activity may be measured, for example, in the manner described hereunder, it is recommended that the isolation and purification of the enzyme be performed while confirming the activity of the enzyme using the assay reaction solution employed in f) in Example 1 hereunder.

EXAMPLES

An example of a method of preparing a DNA sequence, plasmid and transformant according to the present invention will now be described, but the scope of the invention is in no way restricted to this example.

Example 1

The experiment was carried out basically in accordance with *Molecular Cloning, DNA Cloning* and the Takara Shuzo Catalog, mentioned previously. Most of the enzymes used were purchased from Takara Shuzo. The *Bacillus stearothermophilus* used was the known bacterium stored at the American Type Culture Collection (ATCC). Strain ATCC 10149 was used for this experiment.

a) Preparation of chromosomal DNA of *Bacillus stearothermophilus*

Culturing was performed in LB medium (1% tryptone, 0.5% yeast extract, 1% NaCl) at 55° C., and the cells were collected. After suspension in a lysis buffer, lysozyme (chicken albumen-derived, product of Sigma Co.) was added to 10 mg/ml. After lysis, 1/10 volume of 1M Tris.HCl (pH 8.0), 1/10 volume of 10% SDS and 1/50 volume of 5M NaCl were added. Proteinase K (product of Sigma Co.) was added to 10 mg/ml, and the mixture was heated to 50° C.

An equivalent of phenol was added and the mixture stirred and centrifuged to remove the protein. The supernatant was taken with a wide-mouthed pipette into a beaker, and after a 2.5-fold amount of ethanol was gently layered thereon the chromosomal DNA was wound up on a glass rod. After dissolution in TE (10 mM Tris.HCl (pH 8.0), 1 mM EDTA), the DNA was treated with RNaseA (product of Sigma Co.), Proteinase K and phenol, a 2.5-fold amount of ethanol was gently layered thereon and the chromosomal DNA was wound up on a glass rod. After washing with 70% ethanol, it was dissolved in TE and used in the following experiment.

b) Acquisition of pCR64

DNA primers P1 (Sequence No. 4 (SEQ ID NO:4)), P2 (Sequence No. 5 (SEQ ID NO:5)), P4 (Sequence No. 6 (SEQ ID NO:6)), P6 (Sequence No. 7 (SEQ ID NO:7)), P8 (Sequence No. 8 (SEQ ID NO:8)), P9 (Sequence No. 9 (SEQ ID NO:9)), P10 (Sequence No. 10 (SEQ ID NO:10)), P11 (Sequence No. 11 (SEQ ID NO:11)), P12 (Sequence No. 12 (SEQ ID NO:12)) and P13 (Sequence No. 13 (SEQ ID NO:13)) were prepared based on the heretofore known conserved regions of the amino acid sequence of prenyl transferase.

The chromosomal DNA was subjected to partial digestion with Sau3AI, and the PCR (polymerase chain reaction) was conducted with combinations of synthetic DNA P1 and P4, P1 and P6, P1 and P8, P2 and P4, P2 and P6, P2 and P8, P9 and P11, P9 and P4, P9 and P6, P9 and P8, P9 and P13, P1 and P11, P2 and P11, P12 and P4, P12 and P6, P12 and P8, P12 and P13, P1 and P13, P2 and P13, P10 and P4, P10 and p6, P10 and P8, and P10 and P13.

The PCR product of the P10 and P8 combination was linked with the HincII digestion product of plasmid pUC118 (purchased from Takara Shuzo) using T4DNA ligase, and E. coli JM109 was transformed. Plasmids were prepared by the alkali SDS method, and the DNA sequences of 27 clones were analyzed with an Applied Biosystems 373A fluorescent DNA sequencer. One of the sequences was referred as pCR64.

TABLE 1

(Composition of PCR reaction solution)

| | |
|---|---|
| Template DNA | 1 μg |
| 10 × Amplitaq Buffer | 10 μl |
| dNTPs mixture solution (1.25 mM each) | 16 μl |
| Primer 1 | 100 pmol |
| Primer 2 | 100 pmol |
| Taq polymerase adjusted to 100 μl with H₂O | 2 units |

(PCR reaction conditions)

c) Cloning of surrounding region with pCR64 as probe c-1) A DNA fragment consisting of an approximately 500 bp pCR64 digestion product by restriction endonucleases KpnI and HindIII was labelled with DIG using a DIG DNA labeling kit (purchased from BOEHRINGER MANNHEIM). The instructions in the kit manual were followed.

c-2) Preparation of library

The chromosomal DNA was digested with restriction endonuclease AccI, and upon Southern hybridization using the probe from c-1), a band was detected in the position of about 3 kbp. Here, the DNA fragment of about 3 kbp was isolated by agarose gel electrophoresis and treated with T4 DNA polymerase. These were linked with the SmaI digestion product of plasmid pUC18 using T4 DNA ligase, and E. coli JM109 was transformed.

c-3) Screening

The library prepared in c-2) was screened with the probe prepared in c-1). Detection was made using a DIG DNA detection kit (purchased from BOEHRINGER MANNHEIM) and plasmid pAC2 was obtained. The instructions in the kit manual were followed. DNA sequence of the inserted gene of about 2.5 kbp was analyzed with an Applied Biosystems 373A fluorescent sequencer.

d) Isolation of pPR2

The gene library of c-2) was subjected to PCR using a synthetic DNA primer P64-4 (Sequence No. 14 (SEQ ID NO:14)) prepared based on the DNA sequence obtained in c-3) and M13 Primer RV (purchased from Takara Shuzo).

The amplification product was inserted into pT7 Blue T-Vector (purchased from Novagen) to obtain pPR2.

e) Linking of pAC2 and pPR2

DNA fragments of about 1 kbp and 5 kbp as BamHI digestion products of pAC2 and pPR2, respectively, were ligated to obtain pTL6.

f) Measurement of isoprenoid synthetase activity

The E. coli JM105 transformed with pTL6 was cultured overnight in 50 ml of LB medium containing 50 μg/ml of ampicillin, and the cells were collected. These were suspended in 4 ml of lysis buffer and disrupted with ultrasonic waves. Heating was performed at 55° C. for 1 hour to inactivate the E. coli-derived prenyl transferase, and the E. coli-derived denatured protein was removed by centrifugation and the supernatant was used for the assay. The assay reaction mixture was allowed to react for 1 hour or 14 hours at 55° C. The reaction mixture was extracted with 1-butanol, and the radioactivity was measured using a liquid scintillation counter.

TABLE 2

| (Composition of lysis buffer) | |
|---|---|
| Tris.HCl (pH 7.7) | 50 mM |
| EDTA | 1 mM |
| β-Mercaptoethanol | 10 mM |
| PMSF | 0.1 mM |
| (Composition of assay reaction solution (total volume: 1 ml)) | |
| Tris.HCl (pH 8.5) | 50 mM |
| MgCl₂ | 25 mM |
| NH₄Cl | 50 mM |
| β-Mercaptoethanol | 50 mM |
| (all-E)-farnesyl diphosphate | 25 nmoles |
| [1-¹⁴C]Isopentenyl diphosphate (product of Amersham Col., corresponding to approx. 5.5 × 10⁴ dpm) | 25 nmoles |
| Cell-free extract | 500 μl |

Figure 1:
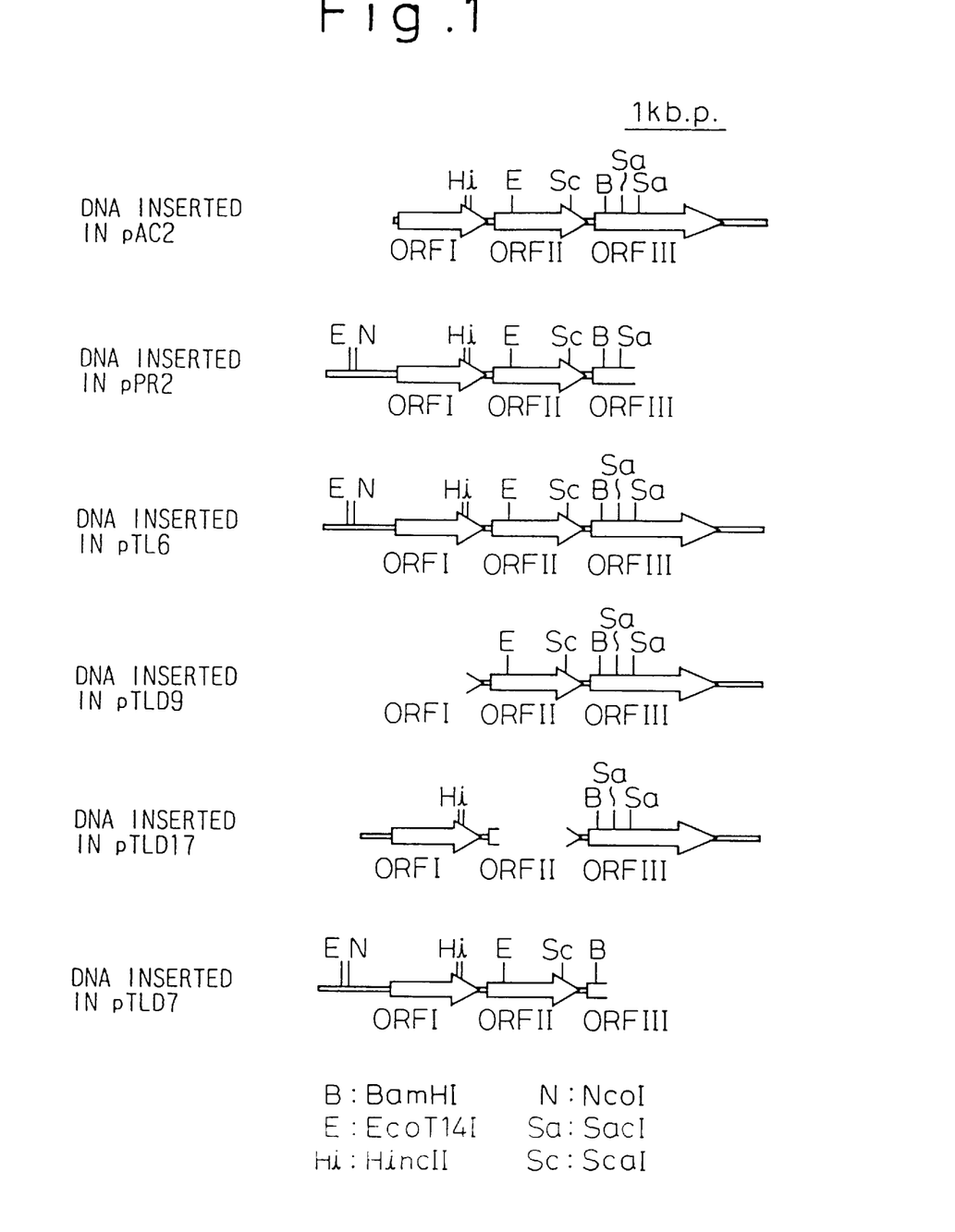
FIG. 1 shows the positional relationships and restriction enzyme maps for plasmids pAC2, pPR2, pTL6, pTLD9, pTLD17 and pTLD7 of the present invention.
Figure 2:
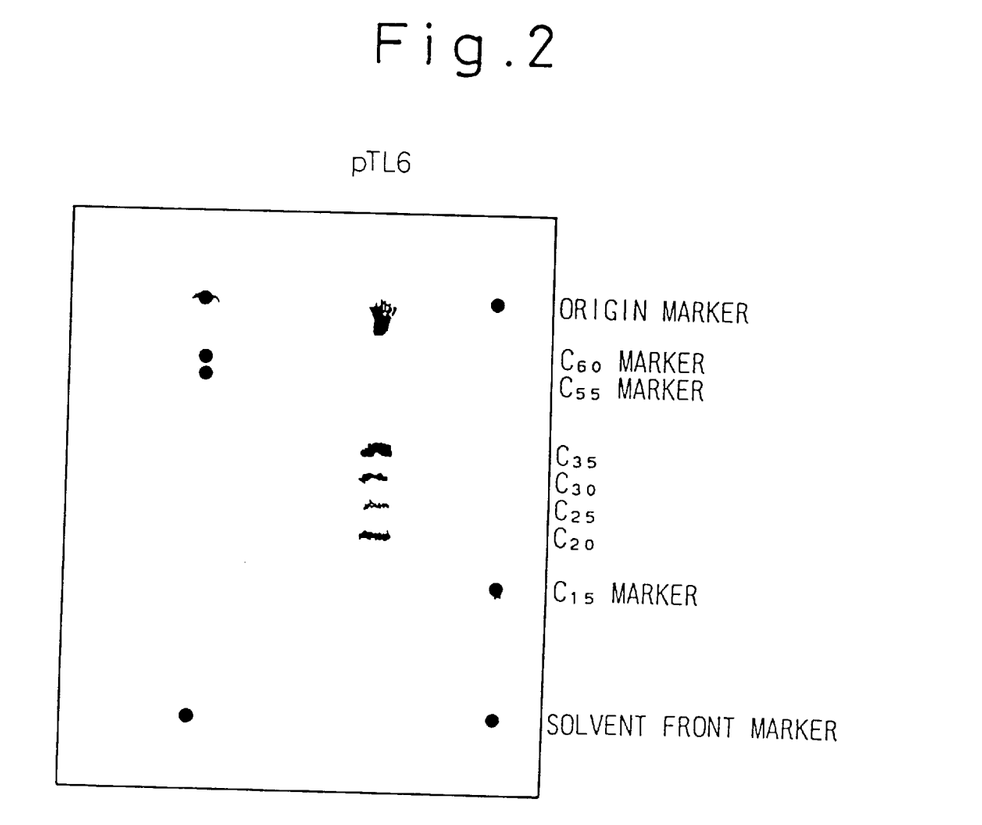
FIG. 2 is a thin layer radiochromatogram of the reaction mixture prepared by incubation of isopentenyl diphospate and farnesyl diphosphate with expression product of a DNA fragment of the present invention.

The 1-butanol extract obtained from the above-mentioned reaction of JM105 carrying pTL6 was hydrolyzed and analyzed by thin-layer chromatography (TLC). As a result, the produced isoprenoid was identified as heptaprenyl diphosphate, thus showing that pTL6 contains the gene for heptaprenyl diphosphate synthetase (FIG. 2). Furthermore, upon investigating the specificity to allylic substrate primers in the assay system described hereunder (Table 3), particular enzyme activity was found with (all-E) farnesyl diphosphate and (all-E) geranylgeranyl diphosphate, whereas dimethylallyl diphosphate, geranyl diphosphate, (2Z, 6E)-farnesyl diphosphate, (2Z, 6E, 10E) geranylgeranyl diphosphate and (2Z, 6E, 10E, 14E) farnesylgeranyl diphosphate were not satisfactory substrates (Table 4).

TABLE 3

| (Composition of assay reaction solution (total volume: 1 ml)) | |
|---|---|
| Tris.HCl (pH 8.5) | 50 mM |
| MgCl₂ | 25 mM |
| NH₄Cl | 50 mM |
| β-Mercaptoethanol | 50 mM |
| Allylic substrate | 2.5 nmoles |
| [1-¹⁴C]Isopentenyl diphosphate (product of Amersham Col., corresponding to approx. 1.1 × 10⁵ dpm) | 0.92 nmoles |
| Cell-free extract | 500 μl |

TABLE 4

Substrate specificity of HDP synthetase derived from DNA sequence of the present invention

| Substrate | Enzyme activity (dpm) |
|---|---|
| Dimethylallyl diphosphate | 324 |
| Geranyl diphosphate | 381 |
| (all-E) Farnesyl diphosphate | 4163 |
| (2Z, 6E) Farnesyl diphosphate | 323 |
| (all-E) Geranylgeranyl diphosphate | 1514 |
| (2Z, 6E, 10E) Geranylgeranyl diphosphate | 648 |
| (all-E) Farnesylgeranyl diphosphate | 728 |
| (2Z, 6E, 10E, 14E) Farnesylgeranyl diphosphate | 281 |

E. coli normally has no heptaprenyl transferase or prenyl transferase with activity at 55° C. E. coli transformed with pTL6 is able to synthesize heptaprenyl diphosphate. Also, the fact that the activity is present at 55° C. indicates that the Bacillus stearothermophilus-derived prenyl transferase encoded by pTL6 is highly thermostable. This also shows that the recombinant is useful for producing stable heptaprenyl diphosphate.

g) Preparation of pTL6 deletion mutants and identification of HDP synthetase gene pTL6 had a gene insert of about 3 kbp, which contained three ORFs. Upon cleavage of pTL6 with restriction endonuclease and preparation of plasmid pTLD9 by deletion of ORFI, plasmid pTLD17 by deletion of OFRII and plasmid pTLD7 by deletion of ORFIII, and measurement of the isoprenoid-synthetase activities, activity was found for pTL6, pTLD9 and pTLD17. 1-Butanol extracts of reaction products of pTL6 and pTLD17 were hydrolyzed and analyzed by TLC, and the produced isoprenoid was confirmed to be heptaprenyl diphosphate.

TABLE 5

HDP synthetase activities derived from DNA sequences of the present invention (Radioactivity of 1-butanol extracts expressed in dpm units)

| Cell-free extract solution | Enzyme activity (dpm) |
|---|---|
| E. coli JM105 | 0 |
| E. coli JM105 / pT7Blue T-Vector | 0 |
| E. coli JM105 / pTL6 | 750 |
| E. coli JM105 / pTLD9 | 16 |
| E. coli JM105 / pTLD17 | 129(*) |
| E. coli JM105 / pTLD7 | 0 |

* = 14 hour reaction

According to the present invention there are provided DNA sequences coding for heptaprenyl diphosphate synthetase enzyme of Bacillus stearothermophilus origin. Recombinant microorganisms, obtained by incorporating the DNA sequences into expression vectors which are then used to transform appropriate E. coli strains, produce safe substances with heptaprenyl diphosphate synthetase activity and heptaprenyl diphosphate.

This effect is achieved by preparing the above-mentioned DNA sequences from chromosomes of Bacillus stearothermophilus, which is not so far taught in scientific literature.

We claim:

1. Isolated DNA containing a base sequence encoding a *Bacillus stearothermophilus* protein having heptaprenyl diphosphate synthetase activity, wherein said DNA is selected from the group consisting of SEQ ID NO. 1, SEQ ID NO. 2, and SEQ ID NO. 3.

2. Isolated DNA having the sequence of SEQ ID NO. 1.

3. Isolated DNA having the sequence of SEQ ID NO. 3.

4. Isolated DNA comprising the sequences of SEQ ID NO. 1 and SEQ ID NO. 3.

5. Isolated DNA comprising the sequences of SEQ ID NO. 1 and SEQ ID NO. 2.

6. Isolated DNA comprising the sequences of SEQ ID NO. 2 and SEQ ID NO. 3.

7. An expression vector comprising the DNA according to claim 1.

8. A host cell transformed by the expression vector according to claim 7.

9. The host cell according to claim 8 which is a bacterium.

10. The host cell according to claim 9 which is Escherichia.

11. A method of producing a peptide with heptaprenyl diphosphate synthetase activity, comprising the steps of culturing a host cell according to claim 8, and recovering from the culture a peptide with heptaprenyl diphosphate synthetase activity.

12. A method of producing heptaprenyl diphosphate, comprising treating an isopentenyl diphosphate, farnesyl diphosphate, geranylgeranyl diphosphate, farnesylgeranyl diphosphate or hexaprenyl diphosphate with a peptide having heptaprenyl diphosphate synthetase activity of claim 11.

13. A method of producing heptaprenyl diphosphate comprising treating an isopentenyl diphosphate, farnesyl diphosphate, geranylgeranyl diphosphate, farnesylgeranyl diphosphate or hexaprenyl diphosphate with a heptaprenyl diphosphate synthetase encoded by a DNA of claim 1, or a preparation containing it.

* * * * *

SEQUENCE LISTING ( 1 ) GENERAL INFORMATION:

( i i i ) NUMBER OF SEQUENCES: 14

( 2 ) INFORMATION FOR SEQ ID NO: 1:

( i ) SEQUENCE CHARACTERISTICS:
        ( A ) LENGTH: 663 base pairs
        ( B ) TYPE: nucleic acid
        ( C ) STRANDEDNESS: double
        ( D ) TOPOLOGY: linear     ( i i ) MOLECULE TYPE: Genomic DNA     ( v i ) ORIGINAL SOURCE:
        ( A ) ORGANISM: Bacillus stearothermophilus     ( x i ) SEQUENCE DESCRIPTION: SEQ ID NO:1:

```
ATG  CTC  GAT  GGC  GCT  TCA  ACG  GCG  CCG  AGT  GAG  GCG  GAG  CCG  TGC  ATC       48
Met  Leu  Asp  Gly  Ala  Ser  Thr  Ala  Pro  Ser  Glu  Ala  Glu  Arg  Cys  Ile
                         5                    10                       15

ATC  GCC  ATG  ATG  CTC  ATG  CAG  ATC  GCC  CTT  GAT  ACC  CAC  GAT  GAG  GTG       96
Ile  Ala  Met  Met  Leu  Met  Gln  Ile  Ala  Leu  Asp  Thr  His  Asp  Glu  Val
                    20                    25                    30

ACA  GAT  GAC  GGC  GGC  GAC  TTG  CGG  GCG  CGG  CAG  CTT  GTC  GTC  CTG  GCC      144
Thr  Asp  Asp  Gly  Gly  Asp  Leu  Arg  Ala  Arg  Gln  Leu  Val  Val  Leu  Ala
               35                    40                    45

GGC  GAC  TTG  TAC  AGC  GGG  CTG  TAC  TAT  GAG  TTG  TTG  GCG  CGT  TCG  GGC      192
Gly  Asp  Leu  Tyr  Ser  Gly  Leu  Tyr  Tyr  Glu  Leu  Leu  Ala  Arg  Ser  Gly
          50                    55                    60

GAA  ACG  GCG  CTC  ATC  CGC  TCG  TTC  GCC  GAG  GCG  GTC  CGC  GAT  ATT  AAC      240
```

-continued

| | | | | | | | | | | | | | | | |
|---|---|---|---|---|---|---|---|---|---|---|---|---|---|---|---|
| Glu | Thr | Ala | Leu | Ile | Arg | Ser | Phe | Ala | Glu | Ala | Val | Arg | Asp | Ile | Asn |
| 65 | | | | | 70 | | | | 75 | | | | | | 80 |

| GAG | CAA | AAA | GTG | CGG | CTT | TAC | GAA | AAA | AAA | GTA | GAG | CGG | ATC | GAG | TCG | 288 |
|---|---|---|---|---|---|---|---|---|---|---|---|---|---|---|---|---|
| Glu | Gln | Lys | Val | Arg | Leu | Tyr | Glu | Lys | Lys | Val | Glu | Arg | Ile | Glu | Ser | |
| | | | | 85 | | | | | 90 | | | | | 95 | | |

| TTG | TTT | GCG | GCG | GTC | GGC | ACG | ATC | GAA | TCG | GCG | TTG | CTT | GTC | AAG | CTC | 336 |
|---|---|---|---|---|---|---|---|---|---|---|---|---|---|---|---|---|
| Leu | Phe | Ala | Ala | Val | Gly | Thr | Ile | Glu | Ser | Ala | Leu | Leu | Val | Lys | Leu | |
| | | | 100 | | | | 105 | | | | | 110 | | | | |

| GCC | GAC | CGC | ATG | GCG | GCG | CCG | CAG | TGG | GGG | CAG | TTT | GCC | TAT | TCG | TAT | 384 |
|---|---|---|---|---|---|---|---|---|---|---|---|---|---|---|---|---|
| Ala | Asp | Arg | Met | Ala | Ala | Pro | Gln | Trp | Gly | Gln | Phe | Ala | Tyr | Ser | Tyr | |
| | | 115 | | | | | 120 | | | | | 125 | | | | |

| TTG | CTG | ATG | CGG | CGC | CTG | CTG | CTC | GAG | CAG | GAA | GCG | TTC | ATC | CGC | ACG | 432 |
|---|---|---|---|---|---|---|---|---|---|---|---|---|---|---|---|---|
| Leu | Leu | Met | Arg | Arg | Leu | Leu | Leu | Glu | Gln | Glu | Ala | Phe | Ile | Arg | Thr | |
| 130 | | | | | 135 | | | | | 140 | | | | | | |

| GGA | GCT | TCG | GTG | CTC | TTT | GAG | CAA | ATG | GCG | CAA | ATC | GCG | TTC | CCG | CGC | 480 |
|---|---|---|---|---|---|---|---|---|---|---|---|---|---|---|---|---|
| Gly | Ala | Ser | Val | Leu | Phe | Glu | Gln | Met | Ala | Gln | Ile | Ala | Phe | Pro | Arg | |
| 145 | | | | | 150 | | | | 155 | | | | | 160 | | |

| GCG | GAA | ACG | TTG | ACG | AAA | GAG | CAA | AAG | CGG | CAT | TTG | CTC | CGC | TTT | TGC | 528 |
|---|---|---|---|---|---|---|---|---|---|---|---|---|---|---|---|---|
| Ala | Glu | Thr | Leu | Thr | Lys | Glu | Gln | Lys | Arg | His | Leu | Leu | Arg | Phe | Cys | |
| | | | | 165 | | | | | 170 | | | | | 175 | | |

| CGC | CGC | TAT | ATC | GAC | GGC | TGC | CGG | GAG | GCG | CTG | TTT | GCG | GCG | AAA | CTG | 576 |
|---|---|---|---|---|---|---|---|---|---|---|---|---|---|---|---|---|
| Arg | Arg | Tyr | Ile | Asp | Gly | Cys | Arg | Glu | Ala | Leu | Phe | Ala | Ala | Lys | Leu | |
| | | | 180 | | | | | 185 | | | | | 190 | | | |

| CCG | GTC | AAC | GGC | CTG | CTG | CAG | CTC | CGC | GTG | GCC | GTG | CTT | TCC | GGC | GGG | 624 |
|---|---|---|---|---|---|---|---|---|---|---|---|---|---|---|---|---|
| Pro | Val | Asn | Gly | Leu | Leu | Gln | Leu | Arg | Val | Ala | Val | Leu | Ser | Gly | Gly | |
| | | 195 | | | | | 200 | | | | | 205 | | | | |

| TTT | CAA | GCC | ATC | GCC | AAA | AAG | ACG | GTG | GAA | GAA | GGG | TAG | | | | 663 |
|---|---|---|---|---|---|---|---|---|---|---|---|---|---|---|---|---|
| Phe | Gln | Ala | Ile | Ala | Lys | Lys | Thr | Val | Glu | Glu | Gly | | | | | |
| 210 | | | | | 215 | | | | | 220 | | | | | | |

( 2 ) INFORMATION FOR SEQ ID NO:2:

( i ) SEQUENCE CHARACTERISTICS:
        ( A ) LENGTH: 705 base pairs
        ( B ) TYPE: nucleic acid
        ( C ) STRANDEDNESS: double
        ( D ) TOPOLOGY: linear     ( i i ) MOLECULE TYPE: Genomic DNA     ( v i ) ORIGINAL SOURCE:
        ( A ) ORGANISM: Bacillus stearothermophilus     ( x i ) SEQUENCE DESCRIPTION: SEQ ID NO:2:

| ATG | CGT | CAA | TCG | AAA | GAA | GAG | CGA | GTC | CAT | CGC | GTA | TTT | GAA | AAC | ATT | 48 |
|---|---|---|---|---|---|---|---|---|---|---|---|---|---|---|---|---|
| Met | Arg | Gln | Ser | Lys | Glu | Glu | Arg | Val | His | Arg | Val | Phe | Glu | Asn | Ile | |
| | | | | 5 | | | | | 10 | | | | | 15 | | |

| TCT | GCG | CAT | TAT | GAC | CGG | ATG | AAC | TCC | GTC | ATC | AGC | TTC | CGC | CGC | CAC | 96 |
|---|---|---|---|---|---|---|---|---|---|---|---|---|---|---|---|---|
| Ser | Ala | His | Tyr | Asp | Arg | Met | Asn | Ser | Val | Ile | Ser | Phe | Arg | Arg | His | |
| | | | 20 | | | | | 25 | | | | | 30 | | | |

| TTG | AAG | TGG | CGC | AAA | GAC | GTG | ATG | CGG | CGG | ATG | AAT | GTG | CAA | AAA | GGC | 144 |
|---|---|---|---|---|---|---|---|---|---|---|---|---|---|---|---|---|
| Leu | Lys | Trp | Arg | Lys | Asp | Val | Met | Arg | Arg | Met | Asn | Val | Gln | Lys | Gly | |
| | | | 35 | | | | | 40 | | | | | 45 | | | |

| AAA | AAA | GCG | CTC | GAT | GTG | TGC | TGT | GGG | ACG | GCT | GAC | TGG | ACG | ATC | GCC | 192 |
|---|---|---|---|---|---|---|---|---|---|---|---|---|---|---|---|---|
| Lys | Lys | Ala | Leu | Asp | Val | Cys | Cys | Gly | Thr | Ala | Asp | Trp | Thr | Ile | Ala | |
| | | 50 | | | | | 55 | | | | | 60 | | | | |

| TTG | GCG | GAG | GCG | GTC | GGT | CCG | GAA | GGG | AAA | GTG | TAC | GGC | CTT | GAT | TTC | 240 |
|---|---|---|---|---|---|---|---|---|---|---|---|---|---|---|---|---|
| Leu | Ala | Glu | Ala | Val | Gly | Pro | Glu | Gly | Lys | Val | Tyr | Gly | Leu | Asp | Phe | |
| 65 | | | | | 70 | | | | 75 | | | | | 80 | | |

| AGC | GAA | AAC | ATG | CTG | AAA | GTC | GGC | GAA | CAG | AAG | GTA | AAA | GCG | CGC | GGG | 288 |
|---|---|---|---|---|---|---|---|---|---|---|---|---|---|---|---|---|
| Ser | Glu | Asn | Met | Leu | Lys | Val | Gly | Glu | Gln | Lys | Val | Lys | Ala | Arg | Gly | |
| | | | | 85 | | | | | 90 | | | | | 95 | | |

| TTG | CAT | AAT | GTG | AAG | CTC | ATT | CAC | GGC | AAT | GCG | ATG | CAG | CTG | CCG | TTT | 336 |
|---|---|---|---|---|---|---|---|---|---|---|---|---|---|---|---|---|

|     |     |     |     |     |     |     |     |     |     |     |     |     |     |     |     |
|-----|-----|-----|-----|-----|-----|-----|-----|-----|-----|-----|-----|-----|-----|-----|-----|
| Leu | His | Asn | Val<br>100 | Lys | Leu | Ile | His<br>105 | Gly | Asn | Ala | Met | Gln<br>110 | Leu | Pro | Phe |
| CCT | GAC | AAT | TCG | TTC | GAT | TAT | GTG | ACG | ATC | GGC | TTC | GGT | TTG | CGC | AAC | 384 |
| Pro | Asp | Asn<br>115 | Ser | Phe | Asp | Tyr | Val<br>120 | Thr | Ile | Gly | Phe | Gly<br>125 | Leu | Arg | Asn |
| GTC | CCT | GAC | TAT | ATG | ACC | GTG | CTT | AAG | GAA | ATG | CAC | CGG | GTG | ACG | AAG | 432 |
| Val | Pro<br>130 | Asp | Tyr | Met | Thr | Val<br>135 | Leu | Lys | Glu | Met | His<br>140 | Arg | Val | Thr | Lys |
| CCG | GGC | GGC | ATA | ACC | GTC | TGC | CTG | GAA | ACG | TCG | CAG | CCG | ACG | CTG | TTC | 480 |
| Pro<br>145 | Gly | Gly | Ile | Thr | Val<br>150 | Cys | Leu | Glu | Thr | Ser<br>155 | Gln | Pro | Thr | Leu | Phe<br>160 |
| GGG | TTT | CGC | CAG | CTT | TAC | TAT | TTT | TAC | TTC | CGG | TTT | ATT | ATG | CCG | CTG | 528 |
| Gly | Phe | Arg | Gln | Leu<br>165 | Tyr | Tyr | Phe | Tyr | Phe<br>170 | Arg | Phe | Ile | Met | Pro<br>175 | Leu |
| TTT | GGC | AAG | CTG | CTG | GCG | AAA | AGC | TAT | GAG | GAG | TAC | TCG | TGG | CTG | CAG | 576 |
| Phe | Gly | Lys | Leu<br>180 | Leu | Ala | Lys | Ser | Tyr<br>185 | Glu | Glu | Tyr | Ser | Trp<br>190 | Leu | Gln |
| GAA | TCG | GCG | CGC | GAG | TTT | CCG | GGG | CGG | GAC | GAG | CTG | GCC | GAG | ATC | TTC | 624 |
| Glu | Ser | Ala<br>195 | Arg | Glu | Phe | Pro | Gly<br>200 | Arg | Asp | Glu | Leu | Ala<br>205 | Glu | Met | Phe |
| CGC | GCC | GCC | GGT | TTT | GTC | GAT | GTC | GAG | GTC | AAA | CCG | TAC | ACG | TTT | GGC | 672 |
| Arg | Ala | Ala<br>210 | Gly | Phe | Val | Asp | Val<br>215 | Glu | Val | Lys | Pro<br>220 | Tyr | Thr | Phe | Gly |
| GTG | GCG | GCG | ATG | CAC | TTG | GGC | TAT | AAA | CGG | TGA |     |     |     |     |     | 705 |
| Val<br>225 | Ala | Ala | Met | His | Leu<br>230 | Gly | Tyr | Lys | Arg |     |     |     |     |     |     |

( 2 ) INFORMATION FOR SEQ ID NO:3:

( i ) SEQUENCE CHARACTERISTICS:
  ( A ) LENGTH: 972 base pairs
  ( B ) TYPE: nucleic acid
  ( C ) STRANDEDNESS: double
  ( D ) TOPOLOGY: linear  ( i i ) MOLECULE TYPE: Genomic DNA  ( v i ) ORIGINAL SOURCE:
  ( A ) ORGANISM: Bacillus stearothermophilus  ( x i ) SEQUENCE DESCRIPTION: SEQ ID NO:3:

|     |     |     |     |     |     |     |     |     |     |     |     |     |     |     |     |     |
|-----|-----|-----|-----|-----|-----|-----|-----|-----|-----|-----|-----|-----|-----|-----|-----|-----|
| GTG | AAC | AAC | ATG | AAG | TTA | AAG | GCG | ATG | TAT | TCG | TTT | TTA | AGC | GAT | GAT | 48 |
| Val | Asn | Asn | Met | Lys<br>5 | Leu | Lys | Ala | Met | Tyr<br>10 | Ser | Phe | Leu | Ser | Asp<br>15 | Asp |
| TTA | GCG | GCG | GTC | GAA | GAG | GAG | CTT | GAG | CGG | GCG | GTT | CAG | TCG | GAA | TAC | 96 |
| Leu | Ala | Ala | Val<br>20 | Glu | Glu | Glu | Leu | Glu<br>25 | Arg | Ala | Val | Gln | Ser<br>30 | Glu | Tyr |
| GGG | CCG | CTT | GGG | GAA | GCG | GCG | CTC | CAT | CTG | TTG | CAG | GCG | GGC | GGA | AAG | 144 |
| Gly | Pro | Leu<br>35 | Gly | Glu | Ala | Ala | Leu<br>40 | His | Leu | Leu | Gln | Ala<br>45 | Gly | Gly | Lys |
| CGG | ATC | CGT | CCC | GTT | TTT | GTC | TTG | CTT | GCC | GCC | CGC | TTC | GGC | CAA | TAT | 192 |
| Arg | Ile<br>50 | Arg | Pro | Val | Phe<br>55 | Val | Leu | Leu | Ala | Ala<br>60 | Arg | Phe | Gly | Gln | Tyr |
| GAC | CTT | GAG | CGG | ATG | AAG | CAT | GTT | GCC | GTT | GCG | CTC | GAG | CTC | ATT | CAT | 240 |
| Asp | Leu<br>65 | Glu | Arg | Met | Lys<br>70 | His | Val | Ala | Val | Ala<br>75 | Leu | Glu | Leu | Ile | His<br>80 |
| ATG | GCT | TCG | CTC | GTC | CAC | GAC | GAT | GTG | ATC | GAC | GAC | GCC | GAT | TTG | CGC | 288 |
| Met | Ala | Ser | Leu | Val<br>85 | His | Asp | Asp | Val | Ile<br>90 | Asp | Asp | Ala | Asp | Leu<br>95 | Arg |
| CGC | GGC | CGG | CCG | ACG | ATC | AAG | GCG | AAA | TGG | AGC | AAC | GCC | TTC | GCC | ATG | 336 |
| Arg | Gly | Arg | Pro<br>100 | Thr | Ile | Lys | Ala | Lys<br>105 | Trp | Ser | Asn | Arg | Phe<br>110 | Ala | Met |
| TAC | ACA | GGG | GAT | TAT | TTG | TTT | GCC | CGC | TCG | CTC | GAA | CGG | ATG | GCG | GAG | 384 |

|  |  |  |  |  |  |  |  |  |  |  |  |  |  |  |  |
|---|---|---|---|---|---|---|---|---|---|---|---|---|---|---|---|
| Tyr | Thr | Gly | Asp | Tyr | Leu | Phe | Ala | Arg | Ser | Leu | Glu | Arg | Met | Ala | Glu |
|  |  | 115 |  |  |  | 120 |  |  |  | 125 |  |  |  |  |  |

| CTC | GGC | AAC | CCG | CGC | GCC | CAT | CAA | GTG | TTG | GCG | AAA | ACG | ATC | GTG | GAA | 432 |
|---|---|---|---|---|---|---|---|---|---|---|---|---|---|---|---|---|
| Leu | Gly | Asn | Pro | Arg | Ala | His | Gln | Val | Leu | Ala | Lys | Thr | Ile | Val | Glu |  |
|  | 130 |  |  |  |  | 135 |  |  |  | 140 |  |  |  |  |  |  |

| GTG | TGC | CGC | GGG | GAA | ATT | GAG | CAA | ATT | AAA | GAC | AAG | TAC | CGG | TTT | GAT | 480 |
|---|---|---|---|---|---|---|---|---|---|---|---|---|---|---|---|---|
| Val | Cys | Arg | Gly | Glu | Ile | Glu | Gln | Ile | Lys | Asp | Lys | Tyr | Arg | Phe | Asp |  |
| 145 |  |  |  |  | 150 |  |  |  |  | 155 |  |  |  |  | 160 |  |

| CAG | CCG | CTG | CGC | ACG | TAT | TTG | CGG | CGC | ATC | CGT | CGG | AAA | ACG | GCG | CTG | 528 |
|---|---|---|---|---|---|---|---|---|---|---|---|---|---|---|---|---|
| Gln | Pro | Leu | Arg | Thr | Tyr | Leu | Arg | Arg | Ile | Arg | Arg | Lys | Thr | Ala | Leu |  |
|  |  |  |  | 165 |  |  |  |  | 170 |  |  |  |  | 175 |  |  |

| CTC | ATC | GCC | GCG | AGC | TGC | CAG | CTT | GGC | GCC | CTC | GCT | GCC | GGC | GCG | CCG | 576 |
|---|---|---|---|---|---|---|---|---|---|---|---|---|---|---|---|---|
| Leu | Ile | Ala | Ala | Ser | Cys | Gln | Leu | Gly | Ala | Leu | Ala | Ala | Gly | Ala | Pro |  |
|  |  |  | 180 |  |  |  |  | 185 |  |  |  |  | 190 |  |  |  |

| GAG | CCG | ATT | GTG | AAG | CGG | CTG | TAC | TGG | TTC | GGC | CAT | TAT | GTC | GGC | ATG | 624 |
|---|---|---|---|---|---|---|---|---|---|---|---|---|---|---|---|---|
| Glu | Pro | Ile | Val | Lys | Arg | Leu | Tyr | Trp | Phe | Gly | His | Tyr | Val | Gly | Met |  |
|  |  | 195 |  |  |  |  | 200 |  |  |  |  | 205 |  |  |  |  |

| TCG | TTT | CAA | ATT | ACC | GAC | GAC | ATT | CTC | GAT | TTC | ACT | GGG | ACG | GAG | GAA | 672 |
|---|---|---|---|---|---|---|---|---|---|---|---|---|---|---|---|---|
| Ser | Phe | Gln | Ile | Thr | Asp | Asp | Ile | Leu | Asp | Phe | Thr | Gly | Thr | GLu | Glu |  |
|  |  | 210 |  |  |  |  | 215 |  |  |  |  | 220 |  |  |  |  |

| CAG | CTC | GGC | AAA | CCG | GCC | GGA | AGC | GAC | TTG | CTA | CAA | GGA | AAC | GTC | ACC | 720 |
|---|---|---|---|---|---|---|---|---|---|---|---|---|---|---|---|---|
| Gln | Leu | Gly | Lys | Pro | Ala | Gly | Ser | Asp | Leu | Leu | Gln | Gly | Asn | Val | Thr |  |
| 225 |  |  |  | 230 |  |  |  |  | 235 |  |  |  |  | 240 |  |  |

| CTT | CCT | GTG | CTG | TAT | GCC | TTG | AGC | GAT | GAG | CGG | GTG | AAG | GCG | GCC | ATT | 768 |
|---|---|---|---|---|---|---|---|---|---|---|---|---|---|---|---|---|
| Leu | Pro | Val | Leu | Tyr | Ala | Leu | Ser | Asp | Glu | Arg | Val | Lys | Ala | Ala | Ile |  |
|  |  |  |  | 245 |  |  |  |  | 250 |  |  |  |  | 255 |  |  |

| GCA | GCT | GTC | GGT | CCG | GAA | ACG | GAC | GTT | GCG | GAA | ATG | GCG | GCG | GTC | ATT | 816 |
|---|---|---|---|---|---|---|---|---|---|---|---|---|---|---|---|---|
| Ala | Ala | Val | Gly | Pro | Glu | Thr | Asp | Val | Ala | Glu | Met | Ala | Ala | Val | Ile |  |
|  |  |  | 260 |  |  |  |  | 265 |  |  |  |  | 270 |  |  |  |

| TCC | GCC | ATT | AAG | CGG | ACG | GAC | GCC | ATT | GAG | CGG | TCG | TAT | GCG | TTA | AGC | 864 |
|---|---|---|---|---|---|---|---|---|---|---|---|---|---|---|---|---|
| Ser | Ala | Ile | Lys | Arg | Thr | Asp | Ala | Ile | Glu | Arg | Ser | Tyr | Ala | Leu | Ser |  |
|  |  | 275 |  |  |  |  | 280 |  |  |  |  | 285 |  |  |  |  |

| GAC | CGT | TAC | CTT | GAC | AAG | GCG | CTT | CAC | CTT | CTT | GAC | GGA | CTG | CCG | ATG | 912 |
|---|---|---|---|---|---|---|---|---|---|---|---|---|---|---|---|---|
| Asp | Arg | Tyr | Leu | Asp | Lys | Ala | Leu | His | Leu | Leu | Asp | Gly | Leu | Pro | Met |  |
|  | 290 |  |  |  |  | 295 |  |  |  |  | 300 |  |  |  |  |  |

| AAT | GAG | GCG | CGC | GGC | CTG | TTG | CGC | GAC | CTC | GCC | CTT | TAC | ATC | GGG | AAA | 960 |
|---|---|---|---|---|---|---|---|---|---|---|---|---|---|---|---|---|
| Asn | Glu | Ala | Arg | Gly | Leu | Leu | Arg | Asp | Leu | Ala | Leu | Tyr | Ile | Gly | Lys |  |
| 305 |  |  |  |  | 310 |  |  |  |  | 315 |  |  |  |  | 320 |  |

| AGG | GAT | TAT | TAA | 972 |
|---|---|---|---|---|
| Arg | Asp | Tyr |  |  |

( 2 ) INFORMATION FOR SEQ ID NO:4:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear     ( i i ) MOLECULE TYPE: Synthetic DNA     ( x i ) SEQUENCE DESCRIPTION: SEQ ID NO:4:

CTNATHCAYG    AYGAYYTNCC    NTCNATGGAC    30

( 2 ) INFORMATION FOR SEQ ID NO:5:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear     ( i i ) MOLECULE TYPE: Synthetic DNA (xi) SEQUENCE DESCRIPTION: SEQ ID NO:5:

GAYAAYGAYG AYYTNMGN-
MG NGGC   24

(2) INFORMATION FOR SEQ ID NO:6:

(i) SEQUENCE CHARACTERISTICS:
        (A) LENGTH: 27
        (B) TYPE: nucleic acid
        (C) STRANDEDNESS: single
        (D) TOPOLOGY: linear     (ii) MOLECULE TYPE: Synthetic DNA     (xi) SEQUENCE DESCRIPTION: SEQ ID NO:6:

ATCRTCNCKD ATYTGRAANG CNARNCC   27

(2) INFORMATION FOR SEQ ID NO:7:

(i) SEQUENCE CHARACTERISTICS:
        (A) LENGTH: 27
        (B) TYPE: nucleic acid
        (C) STRANDEDNESS: single
        (D) TOPOLOGY: linear     (ii) MOLECULE TYPE: Synthetic DNA     (xi) SEQUENCE DESCRIPTION: SEQ ID NO:7:

ATCNARDATR TCRTCNCKDA TYTGRAA   27

(2) INFORMATION FOR SEQ ID NO:8:

(i) SEQUENCE CHARACTERISTICS:
        (A) LENGTH: 21
        (B) TYPE: nucleic acid
        (C) STRANDEDNESS: single
        (D) TOPOLOGY: linear     (ii) MOLECULE TYPE: Synthetic DNA     (xi) SEQUENCE DESCRIPTION: SEQ ID NO:8:

GTCRCTNCCN ACNGGYTTNC C   21

(2) INFORMATION FOR SEQ ID NO:9:

(i) SEQUENCE CHARACTERISTICS:
        (A) LENGTH: 20
        (B) TYPE: nucleic acid
        (C) STRANDEDNESS: single
        (D) TOPOLOGY: linear     (ii) MOLECULE TYPE: Synthetic DNA     (xi) SEQUENCE DESCRIPTION: SEQ ID NO:9:

YTNGARGCNG GNGGNAARMG   20

(2) INFORMATION FOR SEQ ID NO:10:

(i) SEQUENCE CHARACTERISTICS:
        (A) LENGTH: 20
        (B) TYPE: nucleic acid
        (C) STRANDEDNESS: single
        (D) TOPOLOGY: linear     (ii) MOLECULE TYPE: Synthetic DNA     (xi) SEQUENCE DESCRIPTION: SEQ ID NO:10:

| | |
|---|---|
| TA Y WSN Y TNA    THCA Y GA-Y GA | 2 0 |

( 2 ) INFORMATION FOR SEQ ID NO:11:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear     ( i i ) MOLECULE TYPE: Synthetic DNA     ( x i ) SEQUENCE DESCRIPTION: SEQ ID NO:11:

| | |
|---|---|
| Y TCCATRTCN    GCNGC Y TGNC    C | 2 1 |

( 2 ) INFORMATION FOR SEQ ID NO:12:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear     ( i i ) MOLECULE TYPE: Synthetic DNA     ( x i ) SEQUENCE DESCRIPTION: SEQ ID NO:12:

| | |
|---|---|
| Y TNGARTA Y A    THCA Y MGN-CA    Y AARAC | 2 6 |

( 2 ) INFORMATION FOR SEQ ID NO:13:

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: linear     ( i i ) MOLECULE TYPE: Synthetic DNA     ( x i ) SEQUENCE DESCRIPTION: SEQ ID NO:13:

| | |
|---|---|
| DATRTCNARD    ATRTCRTC | 1 8 |

( 2 ) INFORMATION FOR SEQ ID NO:14:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear     ( i i ) MOLECULE TYPE: Synthetic DNA     ( x i ) SEQUENCE DESCRIPTION: SEQ ID NO:14:

| | |
|---|---|
| GATCACATCG    TCGTGGACGA | 2 0 |